United States Patent [19]

Marshall

[11] 4,211,842
[45] Jul. 8, 1980

[54] **STARCH-DEGRADING BENZYMES DERIVED FROM *CLACOSPORIUM RESINAE***

[75] Inventor: James J. Marshall, Miami, Fla.

[73] Assignee: Lifeline Products, Inc., Plainfield, N.J.

[21] Appl. No.: 892,747

[22] Filed: Apr. 3, 1978

[51] Int. Cl.² .............................................. C12D 13/10
[52] U.S. Cl. .................................... 435/210; 435/911; 435/815
[58] Field of Search ............... 195/62, 65, 66 R, 31 R; 435/210, 911

[56] References Cited

PUBLICATIONS

Journal of Dental Research vol. 52 No. 3 p. 573 Jun. 1973.
Chemical Abstracts vol. 75, 84682h (1971).

*Primary Examiner*—Lionel M. Shapiro
*Attorney, Agent, or Firm*—Cooper, Dunham, Clark, Griffin & Moran

[57] ABSTRACT

A novel mixture of starch-degrading enzymes is produced by a strain of *Cladosporium resinae* (Strain ATCC No. 20495). One component of this mixture is a novel exo-α-glucanase (exo-pullulanase). The enzyme mixture is prepared by culturing the microorganism and recovering the enzyme mixture from the medium after removal of grown cells. Exopullulanase can be isolated by fractionation of the mixture. Both the mixture and the exo-pullulanase can be used in the manufacture of dextrose from starch, and alone or in conjunction with appropriate other starch-degrading enzymes, in the production of specific starch conversion products, including fructose syrups. Both the mixture and the exo-pullulanase can also be used for increasing the fermentability of high DE starch conversion products, for example, in production of low calorie alcoholic beverages.

11 Claims, No Drawings

STARCH-DEGRADING BENZYMES DERIVED FROM *CLACOSPORIUM RESINAE*

BACKGROUND OF THE INVENTION

Presently a glucoamylase derived from *Aspergillus niger* is commonly used to degrade starch into dextrose. There are several major disadvantages associated with the use of the *Aspergillus glucoamylase*. The reaction is hindered by the branch points in starch; yields are often lower than desirable; by-products, notably isomaltose, are usually produced and the conversion takes an extended time. Thus, there has been a need for a more efficient enzyme preparation or system for the production of dextrose from starch. The present invention provides a novel mixture of starch-degrading enzymes and a novel exo-pullulanase which are capable of meeting this need.

BRIEF SUMMARY OF THE INVENTION

The present invention relates to a novel and extremely efficient mixture of starch-degrading enzymes produced by a strain of *Cladosporium resinae* (ATCC No. 20495). The invention further concerns a novel exo-α-glucanase herein described as exo-pullulanase which is a component of the novel mixture of starch-degrading enzymes. Additional aspects of the invention relate to methods for culturing the microorganism and for recovering the mixture as well as methods for isolating exopullulanase from the mixture. Finally, the present invention concerns methods of producing dextrose and/or other starch conversion products which involve use of the enzyme mixture and/or of exo-pullulanase.

Accordingly, it is one object of the present invention to provide a method of producing a novel mixture of starchdegrading enzymes from *Cladosporium resinae* (ATCC No. 20495).

It is a related object to provide a novel mixture of starch-degrading enzymes.

A further object is to provide a method of recovering exo-pullulanase from the mixture of starch-degrading enzymes.

A related object of the invention is to provide a novel exo-α-glucanase, exo-pullulanase.

Another object of this invention is to provide methods of using the novel mixture of starch-degrading enzymes and the novel exo-pullulanase in the production of dextrose from starch and in other starch conversion processes.

A final object of the invention is to provide an improved method of preparing low calorie alcoholic beverages.

How these and other objects of the invention are accomplished will be clear upon a reading of the detailed description of the invention and the claims which follow.

DETAILED DESCRIPTION OF THE INVENTION

A species of *Cladosporium resinae* (Strain ATCC No. 20495) has been identified which produces a group of starchdegrading enzymes with a particularly high ratio of pullulanase: amylase activity. A mixture of starch-degrading enzymes can be recovered from the microorganism which has been cultured on a growth medium containing an assimilable carbon source and other nutrients. Starch, glucose and maltose are suitable carbon sources although use of pullulan as the carbon source results in the best production of one component of the enzyme mixture, namely the novel, exo-α-glucanase, exo-pullulanase, described more fully hereinbelow. One suitable medium for culturing *C. resinae* (ATCC No. 20495) is a liquid medium composed of the following:

|  | Grams Per Liter |
|---|---|
| $NH_4NO_3$ | 1.0 |
| $MgSO_4 \cdot 7H_2O$ | 0.3 |
| $KH_2PO_4$ | 1.26 |
| Yeast extract (Difco) | 0.01 |
| Proteose peptone (Difco) | 0.01 |
| Carbon Source | 30.0 |

Cultures are grown on such a medium at a temperature of about 30° C. in shake flasks or in a suitable fermenter for about 10–14 days. The microorganism cells are then removed, e.g. by centrifugation, and the enzyme mixture remaining in the medium is recovered therefrom, e.g. by precipitation upon the addition of ammonium sulfate (75% saturated) or acetone. Enzyme production is stimulated by addition of surfactants, e.g. polyoxyethylene derivatives of fatty acid partial esters of sorbitol anhydrides, e.g. Tween-80, manufactured by Atlas Chemical Industries, Inc. Therefore, about 0.1% of a surfactant such as Tween-80 is regularly added to the growth medium.

Alternatively, the enzyme preparation can be isolated from *Cladosporium resinae* that has been grown on media such as corn steep liquor, that are commonly used for the culturing of fungi to obtain extracellular enzymes. Extremely high yields of the fungus are also obtained by growth on solid media, such as wheat bran, followed by extraction of the culture with water or a salt solution.

Sometimes the enzyme preparation has been found to possess a transferase activity, similar to that produced by *Aspergillus niger*. This transferase activity may be removed by binding to inorganic materials such as bentonite. Except for the removal of the transferase when necessary, it is expected that the enzyme preparation will, for the most part, be used without fractionation, although the levels of individual components might be varied to advantage by culturing the organism under different conditions, e.g. by using different carbon sources.

The component enzymes in the mixture of starchdegrading enzymes can be separated by fractionation of the ammonium sulfate precipitate, e.g. by chromatography on DEAE-cellulose and Sephadex G-100. Five enzymes can be obtained in a pure state, the first four being of well-known types, viz. an α-amylase which has no action on pullulan, an α-glucosidase with high activity on maltose and no action on pullulan, and two glucoamylases similar in substrate specificity to glucoamylase obtained from *Aspergillus niger* but having different chromatographic properties. The fifth enzyme is a novel type of exo-α-glucanase, referred to herein as exo-pullulanase, because of its ability to degrade pullulan at a rapid rate. This novel exo-pullulanase also hydrolyzes one substrate containing α-glucosidic linkages including isomaltose, maltose and amylopectin. Glucose is the sole or major product of its action on all of these substrates. The action of exo-pullulanase on partly oxidized amylose or partially oxidized pullulan showed these polysaccharides were degraded to only very low extents, indicating that the action of the enzyme is of an exo-type. Also, the glucose released from starch and pullulan is in the β-form, as would be expected of an exo-acting glucohydrolase.

The difference between the two exo-α-glucanases, exo-pullulanase, and the glucoamylases similar to the glucoamylase obtained from *Aspergillus niger*, is in their respective abilities to cleave 1, 6-α-glucosidic linkages in starch and starch degradation products.

The relative rates of hydrolysis of glucoamylase from *A. niger* and exo-pullulanase are compared in Table 1, wherein exo-pullulanase is seen to have much greater ability to cleave the 1, 6-linkages in isomaltose, panose, isomaltotriose and dextran.

Table 1

Relative Rates of Substrate Hydrolysis by *Aspergillus niger* Glucoamylase and *Cladosporium resinae* "exo-Pullulanase" (expressed relative to amylopectin as 100).

| Substrate | Cladosporium | Aspergillus |
|---|---|---|
| Amylopectin | 100 | 100 |
| Amylopectin β limit dextrin | 74 | 60 |
| Maltose | 25 | 21 |
| Panose | 24 | 4.8 |
| Pullulan | 20 | 0.3 |
| Isomaltotriose | 3.9 | 0.6 |
| Isolichenin | 2.2 | 0.5 |
| Isomaltose | 2.1 | 0.2 |
| Nigerose | 0.6 | 0.2 |
| Dextran | 0.5 | 0.03 |

The mixture of starch-degrading enzymes is believed to function in the conversion process as follows. α-Amylase serves to enable the exo-acting glucanase to bypass structural anomalies in the substrate, helping to insure that maximum hydrolysis is achieved. The *Aspergillus*-type glucoamylases help to convert linear chains in the substrate into glucose when unhindered by (1→6) linkages. α-Glucosidase has good activity toward isomaltose and hydrolyzes this disaccharide which is produced as a by-product by reversion reactions. The novel exo-pullulanase plays the most important part in starch conversion processes, as it degrades the macromolecular substrate at a fast rate irrespective of the presence of branch points. Using the mixture of starch-degrading enzymes the conversion into glucose can be brought about in a much shorter period of time than the *Aspergillus niger* enzyme preparations.

Comparative studies of the conversion of amylopectin into glucose using *Aspergillus niger* glucoamylase and either the mixture of starch-degrading enzymes or the exo-pullulanase were carried out. When used at the same concentration (measured in terms of ability to release glucose from starch) the mixture or the exo-pullulanase bring about conversion of substrate in about 1/5 to 1/10 of the time which the *Aspergillus niger* enzyme requires to effect the same degree of conversion. Final extents of conversion are: *Aspergillus enzyme*, 92% mixture 98%; and exo-pullulanase, 95%.

The mixture of starch-degrading enzymes from *C. resinae* (ATCC No. 20495) or the exo-pullulanase can be used for the manufacture of dextrose from starch. Starch is preferably first solubilized by acid, enzyme, or acid/enzyme treatment. The concentration of the resulting "solution" should be as high as possible, e.g. 25–30%, and the Dextran Equivalent (DE) of the solubilized starch as low as possible, e.g. 0.5–5, while still maintaining satisfactory rheological properties. The pH of the solution should be in the range 1.5–8.5, preferably 3–4.5.

An amount of the enzyme, either the mixture or the exo-pullulanase, sufficient to convert substantially all of the starch, is added to the solubilized starch. The exact amount of either material which is required depends upon the enzyme preparation used, although amounts in the range 1–30 International Units of activity per milliliter of reaction mixture are usually employed (1 International Unit of activity is the amount that releases 1 μmole of glucose per minute at 37° C. under optimal conditions of starch degradation). For the mixture, use of a final concentration of 5 International Units of activity per milliliter of reaction mixture will typically bring about 95–100% conversion in about 20 hours. Suitable temperatures are in the range 30°–70° C., preferably less than about 55° C., because the enzyme is slightly less thermostable than the Aspergillus enzyme. The enzyme preparation can be modified by immobilization or other means in such a way as to increase thermostability, e.g. on DEAE-cellulose or inorganic carriers. After the conversion is complete the process is completed by standard procedures, e.g., enzyme inactivation, decolorization, crystallization, and removal of the crystallized enzyme.

In addition to its use for the production of dextrose, the enzyme preparation and/or the exo-pullulanase can be used together with glucose isomerase for the production of fructose syrups from starch. The relative thermolability of the enzyme preparation and of the exo-pullulanase renders both preferable to the Aspergillus enzyme in the production of low calorie alcoholic beverages, such as beer. When so used, the enzyme or the enzyme mixture increases the fermentability of high DE starch conversion products in the wort thus bringing about a low carbohydrate, low calorie alcoholic product. Then during pasteurization the enzyme or enzyme mixture is inactivated so that it does not appear in an active form in the final product.

Some distinct advantages of the *Cladosporium resinae* preparation over the *Aspergillus niger* enzyme in starch conversion include:

(a) the ability of one of the *C. resinae* constituents of the enzyme mixture to readily cleave the α-1,6-glucosidic linkages in starch increases the rate and extent of conversion of starch into dextrose over that obtained with the *A. niger* enzyme;

(b) the *C. resinae* enzyme can be used at lower pH;

(c) the presence of an α-glucosidase in *C. resinae* causes breakdown of reversion products, e.g. isomaltose; and (d) the thermolability is advantageous in the case where amylolytic enzymes are to be used for increasing wort fermentability, e.g. in the production of low calorie beers.

As will be clear to anyone skilled in the art, many variations, modifications and alterations may be made in the invention without departing from the spirit and scope thereof.

I claim:

1. A method of producing a mixture of starch-degrading enzymes which comprises:

culturing a microorganism, *Cladosporium resinae* (Strain ATCC No. 20495), on a growth medium containing an assimilable carbon source and other nutrients until starch-degrading enzymes accumulate in the medium;

and recovering the mixture of starch-degrading enzymes from the medium.

2. The method of claim 1 wherein one liter of the growth medium contains 1.0 g $NH_4NO_3$, 0.3 g MgSO$_4$.7 H$_2$O, 1.26 g KH$_2$ PO$_4$, 0.01 g yeast extract, 0.01 g proteose peptone, and 30.0 g of a carbon source.

3. The method of claim 1 wherein the carbon source is pullulan.

4. The method of claim 1 wherein the growth medium is corn steep liquor.

5. The method of claim 1 wherein the growth medium is a solid medium.

6. The method of claim 1 wherein the medium further contains a surfactant.

7. The method of claim 6 wherein the surfactant is a polyoxyethylene derivative of fatty acid partial esters of sorbitol anhydrides.

8. The method of claim 1 wherein said culturing comprises growth of the microorganism at about 30° C. for about 10–14 days, and said recovering comprises removal of the microorganism from the medium by centrifugation and precipitation of the mixture of starch-degrading enzymes remaining in the medium by the addition of ammonium sulfate or acetone.

9. A mixture of exo-pullulanase containing starch-degrading enzymes produced in accordance with the method of claim 1.

10. A method of isolating an exo-pullulanase which comprises chromatographic fractionation of the mixture of starch-degrading enzymes prepared according to the method of claim 1.

11. The exo-pullulanase isolated in accordance with the method of claim 10.

* * * * *